US006117819A

United States Patent [19]

Priesnitz et al.

[11] Patent Number: 6,117,819

[45] Date of Patent: Sep. 12, 2000

[54] HERBICIDE IMPLANTS FOR PLANTS

[75] Inventors: Uwe Priesnitz, Solingen; Jürgen Hölters, Leverkusen; Gunther Penners, Neuss; Bodo Rehbold, Köln; Hans-Jochem Riebel, Wuppertal, all of Germany

[73] Assignee: Bayer Aktiengesellschaft, Leverkusen, Germany

[21] Appl. No.: 09/125,762

[22] PCT Filed: Feb. 17, 1997

[86] PCT No.: PCT/EP97/00727

§ 371 Date: Aug. 25, 1998

§ 102(e) Date: Aug. 25, 1998

[87] PCT Pub. No.: WO97/31528

PCT Pub. Date: Sep. 4, 1997

[30] Foreign Application Priority Data

| | | | |
|---|---|---|---|
| Mar. 1, 1996 | [DE] | Germany | 196 07 850 |
| Mar. 1, 1996 | [DE] | Germany | 196 07 849 |

[51] Int. Cl.[7] ..... A01N 25/34; A01N 57/02

[52] U.S. Cl. ..... 504/206; 504/360

[58] Field of Search ..... 504/206, 360

[56] References Cited

U.S. PATENT DOCUMENTS

| | | | |
|---|---|---|---|
| 3,799,758 | 3/1974 | Franz | 71/86 |
| 4,342,176 | 8/1982 | Wolfe | 47/57.5 |
| 5,086,584 | 2/1992 | Merving | 47/57.5 |
| 5,201,925 | 4/1993 | Itzel et al. | 47/58 |
| 5,340,578 | 8/1994 | Dorworth | 504/117 |
| 5,343,653 | 9/1994 | Itzel et al. | 47/1.5 |
| 5,408,781 | 4/1995 | Merving | 47/57.5 |
| 5,464,627 | 11/1995 | Fu et al. | 424/409 |
| 5,741,521 | 4/1998 | Knight et al. | 424/488 |

FOREIGN PATENT DOCUMENTS

| | | |
|---|---|---|
| 0 564 945 | 10/1995 | European Pat. Off. . |
| 0741 969 | 11/1996 | European Pat. Off. . |
| 2080687 | 2/1982 | United Kingdom . |
| 93/14623 | 8/1993 | WIPO . |

OTHER PUBLICATIONS

Database Sec CH, Wk.8551 AN85–320770 & JP 60–224601 (Dow Chem. Nippon KK) Nov. 9, 1985.

Chemical Abstract, vol. 92, No. 11, Mar. 17, 1980, Abstract No. 89200.

Database Crop, STN International STN—accession No. 97–82206, 1997.

J. Econ. Entomol 61 (month unavailable) 1968, pp. 778–783.

J. Econ. Entomol 64 (month unavailable) 1971, pp. 1295–1298.

J. Econ. Entomol 72 (month unavailable) 1972, ages 51–54.

J. Econ. Entomol 81, (month available) 1988, pp. 1668–1671.

Chem. Abstract, 98:193401 & JP 58–039602, 1983.

*Primary Examiner*—S. Mark Clardy
*Attorney, Agent, or Firm*—Joseph C. Gil

[57] ABSTRACT

The present invention provides a solid shaped plant treatment product, a process for preparation of the product, and a method for use of the product in treating individual plants. The solid shaped plant treatment product contains a systemic herbicide which includes a herbicidally active compound homogeneously distributed in a polymeric carrier material. Suitable polymeric carrier materials bind the active compound in a solid form. The solid shaped plant treatment product can be implanted into a target plant in this form. Particularly, the solid shaped form is introduced into the vicinity of the vascular bundle system of the plant to be destroyed.

1 Claim, No Drawings

HERBICIDE IMPLANTS FOR PLANTS

TECHINAL FIELD OF THE INVENTION

The invention relates to novel plant treatment products based on systemic herbicides which are incorporated into solid shaped bodies and can be implanted into the target plants in this form, to processes for their preparation, and to methods for treating individual plants with systemic herbicides which are incorporated into solid shaped bodies and which are introduced into the plants' vascular bundle system in this form, thus allowing in particular trees and also other undesired plants to be destroyed.

BACKGROUND OF THE INVENTION

It is already known to introduce solutions of certain agents for controlling pests, or "pesticides" (in particular insecticides), into trees by means of so-called trunk implantation (cf. J. Econ. Entomol 61 (1968), 778–783; loc. cit. 64 (1971), 1295–1298; loc. cit. 72 (1979), 51–54; loc. cit. 81 (1988), 1668–1671; U.S. Pat. No. 4,342,176).

It is also known to use such active compounds, incorporated into solid shaped articles, for controlling pests on certain plants, in particular on trees (cf. EP 564945, JP 58039602—cited in Chem. Abstracts 98: 193401).

There is furthermore known a device for the transcuticular application of active compounds to plants in the form of an active-compound support which stores the active compound (cf. EP 254196). Upon use, however, this active-compound support is located on the surface of the plant and not inside the plant.

There is also known a method, or device, for applying herbicides to trees, in which the active compound is introduced into the tree via a sort of punch hammer (cf. U.S. Pat. No. 5,086,584). However, this application method is relatively complex; there was therefore a demand for a simpler use form for destroying undesired trees and other plants.

To destroy undesired plants, herbicides are furthermore generally employed in formulated form, that is to say combined with certain additives, with the aid of mechanical application equipment—in most cases spray equipment.

The task of removing undesired trees and shrubs from woodland or from gardens and parks is apparently gaining in importance. Performing this task with the aid of mechanical means is only possible on small areas in practice, and even that requires a great deal of labour, expense and technical effort. While the use of herbicides via spray application is technically feasible, it is unsatisfactory from the environmental angle.

SUMMARY OF THE INVENTION

The invention relates to the following:

(1) solid shaped plant treatment products comprising systemic herbicides, which comprise the herbicidally active compounds homogeneously distributed in a polymeric support material as binder and which can be introduced into the vicinity of the vascular bundle system of individual plants to be destroyed;

(2) processes for the preparation of solid shaped plant treatment products according to (1) which can be introduced into the vicinity of the vascular bundle system of individual plants, characterized in that systemic herbicidally active compounds are polymerized or mixed with polymeric supports and then shaped;

(3) method for treating individual plants with systemically active herbicides, characterized in that solid shaped plant treatment products according to (1) which comprise systemic herbicides, where herbicidally active compounds within a polymeric support material as binder are introduced into the vicinity of the vascular bundle system of the plants to be destroyed.

Surprisingly, the treatment method according to the invention allows undesired trees and shrubs to be removed in a very simple manner. The plant treatment products according to the invention can be introduced or "implanted", or "grafted", into small holes in the target plants which have been produced using customary manual drills. The treatment method according to the invention is distinguished by especially simple handling—expensive "special equipment" is not required—and by application of the active compound precisely at the location where the action is desired, avoiding undesired contamination of the environment. With a view to the application of herbicides which is otherwise customary practice, the novel application option which has now been found represents a valuable enrichment of the prior art, both from economical and ecological perspectives.

The invention preferably relates to solid shaped plant treatment products comprising systemic herbicides, in the form of "shaped articles" or "implants" which comprise the active compounds and which are introduced into the target plants, whereupon the implants are dissolved by the sap and are distributed in the plants.

The invention preferably relates to solid shaped plant treatment products which comprise systemic herbicides and where the active compounds are selected from among the herbicidally active compounds which are normally used for destroying undesired plants in the semi-selective or in the non-selective field of weed control, and which are commercially available.

As has additionally been found, certain N-phosphonomethyl-glycine esters (which are not yet commercially available) are also outstandingly suitable as active compounds for this novel purpose.

DETAILED DESCRIPTION OF THE INVENTION

In particular, the invention relates to solid shaped plant treatment products which comprise herbicides and where the active compounds are selected from amongst the group of substances below (termed by the scientific names and, if appropriate, the common names):

γ-(hydroxymethylphosphinyl)-L-α-aminobutyryl-L-alanyl-L-alanine ("bialaphos"), 2-amino-4-(hydroxymethylphosphinyl)-butyric acid ("glufosinate"), N-phosphonomethyl-glycine ("glyphosate"), and N-phosphonomethyl-glycine esters of the general formula (I)

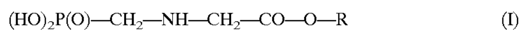

$$(HO)_2P(O)—CH_2—NH—CH_2—CO—O—R \qquad (I)$$

in which

R represents straight-chain or branched alkyl having 1 to 10 carbon atoms, preferably having 2 to 6 carbon atoms.

In addition to these "pure active compounds" it is also possible to use conventionally used salts of these compounds, for example sodium, potassium, ammonium, methyl ammonium, ethyl ammonium, n- or i-propylammonium, n-, i-, s- or t-butylammonium, cyclopentylammonium, cyclohexylammonium, dimethylammonium, diethylammonium, di-n- propylammonium, di-i-propylammonium, dibutylammonium, dicyclopentyl-ammonium and dicyclohexylammonium salts, and also trimethylsulphonium and triethylsulphonium salts in the plant treatment products according to the invention. An example of such a salt which may be mentioned is the trimethylsulphonium salt of N-phosphonomethyl-glycine (common name: "sulphosate").

Adducts of the abovementioned active compounds with acids, that is to say addition products of these compounds with acids, for example with hydrochloric acid (hydrogen chloride), hydrogen bromide, sulphuric acid, phosphoric acid, methanesulphonic acid, ethanesulphonic acid, propanesulphonic acid, butanesulphonic acid, benzenesulphonic acid and p-toluenesulphonic acid, may also be used in the plant treatment products according to the invention.

The N-phosphonomethyl-glycine ester of the formula (I) to be used in accordance with the invention are already known and/or can be prepared by processes known per se; also, it is known that N-phosphonomethyl-glycine esters have herbicidal properties (cf. DE 2 152 826, DE 2 166 573, U.S. Pat. No. 3,977,860).

The N-phosphonomethyl-glycine esters of the general formula (I) are obtained when N-phosphonomethyl-glycine of the formula (II)

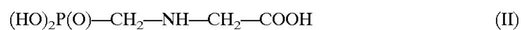

$$(HO)_2P(O)—CH_2—NH—CH_2—COOH \quad (II)$$

is reacted with an alcohol of the formula (III)

in which

R has the abovementioned meaning in the presence of an acid such as, for example, hydrogen chloride at temperatures between 40° C. and 150° C., and the resulting acid adduct of the compound of the formula (I) is reacted with an acid binder such as, for example, triethylamine or propylene oxide at temperatures between 0° C. and 60° C., if appropriate after intermediate isolation (cf. the preparation examples).

The invention relates to a novel use of systemically acting herbicides by means of shaped bodies which are introduced into trees and shrub-like plants in order to destroy them. These "implants" are taken up by the sap and distributed in the plant.

The invention preferably relates to a novel use of semi-selectively or non-selectively acting systemic herbicides.

In particular, the invention relates to a novel use of systemic herbicides from the series consisting of bialaphos, glufosinate, glyphosate and of salts of these compounds, and to the novel use of N-phosphonomethyl-glycine ethyl ester.

In accordance with the invention, the implant is brought into intimate contact with the target plant, so that the active compound which it comprises reaches the plant via the sap and is distributed within the plant via the metabolism.

The implants according to the invention preferably consist of the pure active compound and a suitable binder for shaping.

Surprisingly, the pure active compounds can be employed for destroying undesirable plants directly in solid form with small amounts of binder without a combination with the formulation auxiliaries which are otherwise customary, and without use of specific applicators and/or dispensers.

Suitable binders are those which are capable of accommodating and binding the active compound in solid form. These include natural and synthetic polymers and latices.

A preferred embodiment of the shaped bodies or implants according to the invention has a rod-shaped structure.

The active compound can be embedded in a polymer in the form of microcapsules, or exist within a matrix.

Polymers which are suitable for making the support for the active compound are, for example, polyvinyl alcohol, polyvinyl acetate, plastified polyvinyl chloride, plastified polyamide, polyethylene oxide, polypropylene oxide, gelatine, waxes, polysucroses, polymers of acrylic acid or methacrylic acid, polyhydroxyalkyl acrylates, or silicone rubbers.

The following may be mentioned as polymeric binders:

polyolefins such as polyethylene, polypropylene and polyisobutylene, vinyl polymers such as polyvinyl chloride (PVC), polyvinyl alcohol, polyvinyl ethers, homo- and copolymers of N-vinyl-pyrrolidone such as polyvinylpyrrolidone and N-vinylpyrrolidone/vinyl acetate copolymers, polyvinyl acetate, polystyrene and polyacrylonitrile, acrylic and methacrylic polymers, homo- and copolymers of acrylic acid and/or methacrylic acid and their salts, polyamides, polycarbonates, polyacetals, epoxy resins, polyesters, polyurethanes, polyalkylene terephthalates, polyaryl ethers and polyimides and mixtures of these polymers.

Further possible binders which may be mentioned are copolymers of olefin/vinyl esters such as ethylene/vinyl acetate copolymers, ethylene/vinyl alcohol copolymers, olefin/acrylate and olefin/methacrylate copolymers such as ethylene/acrylic acid copolymers, ethylene/methacrylate copolymers and ethylene/ethyl acrylate copolymers, and also ABS copolymers, styrene/acrylonitrile copolymers, styrene/butadiene copolymers and olefin/maleic anhydride copolymers such as ethylene/maleic acid anhydride copolymers.

Other possible binders which may be mentioned are starch polymers such as natural starch and amylose, mixtures of starch polymers and thermoplasts, sugar polymers such as polymaltoses, celluloses and cellulose derivatives such as methylcelluloses; cellulose esters, cellulose ethers, cellulose ether esters and cellulose nitrates, polyalkylated or polyoxyalkylated celluloses and esters thereof, polycarboxyalkylated celluloses and their alkali metal salts and esters; hydrogels such as alginates: natural resins such as colophonium, gum arabic and agar agar.

Other polymeric support materials which may be mentioned are thermoplastic elastomers. These are materials which contain elastomeric phases in thermoplastically processable polymers, either as a physical admixture or chemically bonded. Polyblends, in which the elastomeric phases exist in the form of a physical admixture, are distinguished from block copolymers, in which the elastomeric phases form part of the polymeric skeleton. The structure of the thermoplastic elastomers means that hard and soft zones coexist next to each other. The hard zones form a crystalline reticulated structure or a continuous phase whose interstices are filled up with elastomeric segments. Due to this structure, these materials have rubber-like characteristics.

There are five main groups of different thermoplastic elastomers which may preferably be mentioned here:

copolyesters, polyether block amides (PEBA), thermoplastic polyurethanes (TPU), thermoplastic polyolefins (TPO), styrene block copolymers.

Others which may be mentioned as being preferred are polymers which can be degraded by photochemical processes such as, for example, ethylene/CO copolymers, vinylketone copolymers and polymers which comprise additives which initiate photochemical degradation.

Especially preferred polymers are biodegradable polymers, i.e. polymers which can be degraded by natural processes, such as, for example, starch polymers and mixtures of starch polymers and thermoplasts, sugar polymers, celluloses and cellulose derivatives, polyoxyalkylated celluloses and starches, hydrogels such as alginates, naturally occurring resins such as colophonium, gum arabic and agar agar, homo- and co-polymers of lactic acid such as polylactides and polylactide glycosides, and also polyglycosides, polycaprolactones and polymers from the group of the polyhydroxyalkanoates such as poly-3-hydroxybutyric acid (PHB) and copolymers of 3-hydroxy-butyric acid with 3-hydroxy-valeric acid (PHBV).

Very specially preferred are water-soluble polymers and polymers which are swellable in water, such as polyvinyl alcohol, polyvinyl alkyl ethers, homo- and co-polymers of N-vinyl-pyrrolidone, homo- and co-polymers of acrylic acid and of methacrylic acid and salts thereof, polyalkylene oxide ethers, polyalkylated celluloses, polyoxyalkylated celluloses, polycarboxyalkylated celluloses and derivatives thereof, starches and hydrogels.

Typical vinyl polymers or vinyl resins are polyvinyl halides such as polyvinyl chloride, polyvinyl chloride/vinyl acetate and polyvinyl fluoride, polyacrylate and polymethacrylate esters, such as polymethyl acrylate and polymethyl methacrylate, and also polystyrene and polyvinyltoluene.

Plasticizers which are suitable for preparing the shaped bodies based on polyvinyl resin are those which are normally used for plasticizing solid vinyl resins. The plasticizer to be employed depends on the resin and its compatibility with the plasticizer. Suitable plasticizers are phosphonic esters such as tricresol phosphate, phthalic esters such as dimethyl phthalate and dioctyl phthalate, and adipic esters such as diisobutyl adipate. Other esters such as the esters of azelaic acid, maleic acid, ricinoleic acid, myristic acid, palmitic acid, oleic acid, sebacic acid, stearic acid and trimellitic acid, and complex linear polyesters, polymeric plasticizers and epoxidized soya oils may also be used. The plasticizer amounts to approximately 10 to 50% by weight, preferably approximately 20 to 45% by weight, of the entire composition.

The shaped bodies may also comprise further components such as stabilizers, lubricants, fillers and colours, without these altering the basic properties of the composition. Suitable stabilizers are antioxidants and agents which protect the shaped body against ultraviolet radiation and undesired degradation during processing (such as extruding). Some stabilizers such as epoxidized soya oils additionally act as secondary plasticizers. Lubricants which can be used are, for example, stearates, stearic acid and low-molecular-weight polyethylene. These components can be used at a concentration of up to approximately 20% by weight of the entire composition. Preferred polymers from the group of polycondensates are polyamides and/or polyesters with a melting point or softening point between 50° C. and 160° C. Especially preferred polyamides are homo- or co-polyamides of ω-amino-caproic acid, ω-amino-oenanthic acid, ω-amino-caprylic acid, ω-amino-pelargonic acid, ω-amino-capric acid, ω-amino-undecylic acid, ω-amino-lauric acid and/or caprolactam, lactam-7, lactam-8, lactam-9, lactam-10, lactam-11 or lauryllactam and/or dimethylenediamine, trimethylenediamine, tetramethylenediamine, pentamethylenediamine, hexamethylenediamine, polyether diamine, and also oxalic acid, malonic acid, succinic acid, glutaric acid, adipic acid, pimelic acid, suberic acid, azelaic acid, sebacic acid, nonanedicarboxylic acid, decanedicarboxylic acid, undecanedicarboxylic acid, dodecanedicarboxylic acid and dimerized fatty acids. Very especially preferred are polymers of caprolactam, lauryllactam, ω-amino-lauric acid, ω-amino-caproic acid, hexamethylenediamine, polyether diamine, adipic acid, dimerized fatty acids or mixtures of these. Especially preferred polyesters are homo- or co-polyesters of ω-hydroxy-acetic acid, ω-hydroxy-propionic acid, ω-hydroxy-butyric acid, ω-hydroxy-valeric acid, ω-hydroxy-caproic acid, ω-hydroxy-oenanthic acid, ω-hydroxy-caprylic acid, ωhydroxy-pelargonic acid, ω-hydroxy-capric acid, ω-hydroxy-undecylic acid, ω-hydroxy-lauric acid and/or caprolactam, lactone-7, lactone-8, lactone-9, lactone-10, lactone-11, lauryllactone and/or ethylene glycol, propanediol, butanediol, pentanediol, hexanediol, a mixture of aliphatic diols having 2 to 18 carbon atoms, and also oxalic acid, malonic acid, succinic acid, glutaric acid, adipic acid, pimelic acid, suberic acid, azelaic acid, sebacic acid, nonanedicarboxylic, decanedicarboxylic acid, undecanedicarboxylic acid, dodecanedicarboxylic acid, terephthalic acid, isophthalic acid and/or anhydrides thereof and/or chlorides thereof and/or esters thereof.

Polyurethanes are prepared in a manner known per se by reacting isocyanates with higher-molecular-weight compounds which have at least two groups which are reactive towards isocyanates, and, if appropriate, low-molecular-weight chain extenders and/or monofunctional chain terminators (cf. S. H. Saunders, K. C. Frisch; Polyurethanes, Part 1, High Polymer Science XVI, Interscience Publishers, New York 1962).

Suitable starting materials for the preparation of the polyurethanes are aliphatic, cycloaliphatic, araliphatic, aromatic and heterocyclic polyisocyanates as they are described, for example, by W. Siefken in Liebigs Annalen der Chemie 562, pages 75 to 136. The following may be mentioned by way of example:

Ethylene diisocyanate, 1,4-tetramethylene diisocyanate, 1,6-hexamethylene diisocyanate, 1,12-dodecane diisocyanate, cyclobutane 1,3-diisocyanate, cyclohexane 1,3-diisocyanate, cyclohexane 1,4-diisocyanate and any mixtures of these compounds, 1-isocyanato-3,3,5-trimethyl-5-isocyanatomethyl-cyclohexane (cf. DE 1202785, U.S. Pat. No. 3,401,190), 2,4- and 2,6-hexahydrotoluene diisocyanate and any mixtures of these, hexahydro-1,3- and -1,4-phenylene diisocyanate, perhydro-2,4'- and/or -4,4'-diphenylmethane diisocyanate, 1,3- and 1,4-phenylene diisocyanate, 2,4- and 2,6-toluylene diisocyanate and any mixtures of these compounds, diphenylmethane 2,4'- and/or -4,4'diisocyanate, naphthylene-1,5-diisocyanate, triphenylmethane 4,4',4"-triisocyanate, polyphenyl polymethylene polyisocyanate as they are obtained by aniline/formaldehyde condensation and subsequent phosgenation (cf. GB 874430, GB 848671), m- and p-isocyanatophenylsulphonyl isocyanate (cf. U.S. Pat. No. 3,454,606), perchlorinated arylpolyisocyanate (cf. DE 1157601, U.S. Pat. No. 3,277,138), diisocyanate (cf. U.S. Pat. No. 3,492,330), polyisocyanates having allophanate groups (cf. GB 99489, DE 761626), polyisocyanates having isocyanurate groups (cf. U.S. Pat. No. 3,001,973, DE 1022789, DE 1222067, DE 1027394, DE 1929034, DE 2004048), polyisocyanates having urethane groups (cf. DE 752261, U.S. Pat. No. 3,394,164), polyisocyanates having acylated urea groups (cf. DE 1230778), polyisocyanates having biurete groups (cf. DE 1101394, U.S. Pat. No. 3,124,605, U.S. Pat. No. 3,201,372, GB 889050), polyisocyanates prepared by telomerization reactions (cf. U.S. Pat. No. 3,654,106), polyisocyanates having ester groups (cf. GB 965474, GB 1072956, U.S. Pat. No. 3,567,763, DE 1231688), reaction products of the above-mentioned isocyanates with acetals (cf. DE 1072385), and polyisocyanates containing polymeric fatty acid radicals (cf. U.S. Pat. No. 3,455,883).

It is also possible to employ the distillation residues which are obtained during industrial isocyanate production and which have isocyanate groups, as appropriate in the form of a solution in one or more of the abovementioned polyisocyanates. It is furthermore possible to use any mixtures of the abovementioned polyisocyanates.

Preferred polyisocyanates are generally products based on toluylene diisocyanate and diphenylmethane diisocyanate.

Other starting materials for the preparation of the polyurethanes are compounds having at least two hydrogen atoms which are reactive towards isocyanates, having a molecular weight of, as a rule, 400 to 10,000. These are to be understood as meaning not only compounds which have amino groups, thiol groups or carboxyl groups, but preferably polyhydroxyl compounds, in particular compounds having 2 to 8 hydroxyl groups, specifically those of molecular weight 800 to 10,000, preferably 1,000 to 6,000, polyesters which have, for example, 2 to 8, preferably 2 to 4, hydroxyl groups, polyethers, polythioethers, polyacetals, polycarbonates and polyester amides as they are known for the preparation of homogeneous and of cellular polyurethanes.

Photochemically degradable polymers are polymers which contain groups which are sensitive to UV light, or polymers which contain additives which initiate photochemical reactions.

Copolymers of ethylene and carbon monoxide (cf. U.S. Pat. No. 2,495,286, DE 2316697, DE 3921144) may be mentioned as polymers containing groups which are sensitive to UV light. Mention may also be made of copolymers of vinyl monomers with keto groups such as, for example, methyl vinyl ketone, methyl isopropenyl ketone and ethyl vinyl ketone, with, for example, polyolefins such as ethylene, propylene and vinyl compounds such as, for example, styrene and methyl methacrylate (cf. U.S. Pat. No. 3,759,952, U.S. Pat. No. 3,811,931, U.S. Pat. No. 3,860,538, U.S. Pat. No. 3,878,169). Such products can be obtained, for example, under the name Ecolyte and can be used directly as polymeric support materials or, preferably, as a mixture with other polymers.

Polymers which contain additives as photodegradation initiators are preferably used on the basis of polyolefins such as polyethylene, polybutylene and vinyl resins such as polystyrene and PVC. Photoreactive additives are preferably organic carbonyl compounds such as, for example, aromatic aldehydes, ketones, diketones and quinones. Benzophenone and its derivatives are especially preferred. Another group of preferred photoreactive additives are inorganic or organic salts such as chlorides, stearates and octanoates of transition metals such as iron, nickel, cobalt, copper and manganese. Organic complexes of transition metals such as ferrocene and dithiocarbamates of iron and magnesium may also be used.

Especially suitable starch polymers are those which can be processed in thermoplasts and mixtures of starch polymers and thermoplasts. The thermoplasts preferably contain admixtures of photochemically degradable polymers.

Starch which can be processed as thermoplast is, for example, natural starch which contains water as plasticizer (cf. EP 118240), destructured starch (cf. EP 304401, EP 391853) or hydroxyalkoxylated starch such as, for example, hydroxyethyl- and hydroxypropyl-substituted starch. High-amylose starches which contain plasticizer can also be processed as thermoplasts (cf. DE 4013344). Preferred plasticizers are alcohols having several hydroxyl groups, for example glycerol, diethylene glycol, triethylene glycol, sorbitol and polyvinyl alcohol.

Starch polymer/thermoplast mixtures which can be used according to the invention include mixtures which comprise 6 to 15 parts by weight of starch in addition to, for example, PVC, ethylene/vinyl acetate copolymers, polyurethanes, polyolefins such as polypropylene and, in particular, polyethylene, for example those which are obtainable under the names Ecostar, Polyclean, Amyplast and Polygrade. Mixtures of starch with homo- and co-polyesters such as poly-caprolactone and with thermoplastic polyurethanes are preferred. The starch used for mixtures with thermoplasts can be surface-treated, for example with silanes; alternatively, it can be dried and employed without further modification. The mixtures can also comprise additives. These are, for example, unsaturated compounds such as unsaturated fatty acid esters, for example soya oil, styrene/butadiene block copolymers, natural rubber and organic salts of transition metals such as, for example, cobalt naphthenate, and known antioxidants.

Mixtures of starch polymers and thermoplasts where the starch amounts to up to 95% by weight which are obtained, for example, by mixing starch with polymers which contain carboxyl groups such as, for example, ethylene/acrylic acid copolymers, can also be used according to the invention as binders (for the preparation, cf. EP 404727).

Also suitable as binders are mixtures of starch polymers and thermoplasts which are obtained from grafted copolymers of starch with, for example, maleic anhydride and vinyl monomers such as styrene, acrylonitrile and acrylic and methacrylic monomers such as, for example, methyl methacrylate. Also suitable are copolymers which are obtained by polymerizing ethylene in the presence of starch modified with Ziegler-Natta-catalysts (cf. DE 3007433).

Also suitable as polymeric support materials or binders are known celluloses and cellulose derivatives, for example cellulose esters such as cellulose acetate, cellulose propionate, cellulose butyrate and mixed esters such as cellulose acetobutyrate, furthermore cellulose ethers such as methyl cellulose, ethyl cellulose, hydroxyethyl cellulose and sodium carboxymethyl cellulose, and also cellulose nitrate.

Preferred binders are those which can be processed as thermoplasts and/or naturally degradable material, for example mixtures of cellulose esters such as cellulose acetate and/or cellulose acetobutyrate, with biodegradable additives such as, for example, carboxylic esters which contain a few ester and/or hydroxyl groups, for example esters of citric acid, tartaric acid or succinic acid (cf. EP 394803). Organometal compounds such as, for example, iron(II) acetylacetonate or bis-(cyclopentadienyl)-iron or derivatives thereof may additionally be added to the mixtures to improve their degradability.

Especially preferred polymeric binder or support materials are cellulose/lactone graft copolymers such as, for example, cellulose polyhydroxyhexanoate and cellulose ether esters such as, for example, hydroxypropylcellulose phthalate.

Polyhydroxylalkanoates are polymers of aliphatic and aromatic hydroxycarboxylic acids which are formed by prokaryotic microorganisms and which can be prepared by fermentation processes (cf. EP 15669, EP 46344, EP 52459).

Examples of suitable polyhydroxyalkanoates are polymers of 4-hydroxy-butyric acid, 4-hydroxy-valeric acid and 5-hydroxy-valeric acid, of 3-hydroxy derivatives of carboxylic acids such as propionic acid, butyric acid, valeric acid, hexanoic acid, heptanoic acid, octanoic acid, nonanoic acid, decanoic acid, undecanoic acid, dodecanoic acid, 4-methyl-hexanoic acid, 5-methyl-hexanoic acid, 5-methyl-octanoic acid, 6-methyl-octanoic acid and 7-methyl-octanoic acid, of 3-hydroxy derivatives of unsaturated carboxylic acids such as crotonic acid, 4-pentanoic acid, 4-hexanoic acid, 5-hexanoic acid, 6-octenoic acid, 7-octenoic acid, 8-nonenoic acid, 9-decenoic acid, 6-dodecanoic acid, 5-tetradecanoic acid and 5,8-tetradecadienoic acid, and of 3-hydroxy derivatives of halogenocarboxylic acids such as 6-bromo-hexanoic acid, 6-chloro-hexanoic acid, 7-fluoro-heptanoic acid, 8-bromo-octanoic acid, 9-fluoro-nonanoic acid and 11-bromo-undecanoic acid.

Preferred polymeric binders or support materials are homo- and copolymers of 3-hydroxy-butyric acid and copolymers thereof with 3-hydroxy-valeric acid. Such products are obtainable under the name Biopol.

Fillers and/or additives which the polymeric binders or support materials may contain are known fillers/additives conventionally used in practice, or inorganic- or organic-based fibres, colouring agents such as dyestuffs and coloured pigments, water binders, surfactants or pH stabilizers.

Inorganic fillers which may be mentioned are baryt, titanium dioxide, quartz sand, precipitated silicas, kaolin, soot and glass (micro)beads, and suitable organic fillers which may be mentioned are polystyrene- or PVC-based powders.

Examples of suitable fibres are glass fibres of 0.1 mm to 1 mm in length, or organic fibres such as polyester or polyamide fibres.

Customary inorganic- or organic-based coloured pigments or dyestuffs may be used for achieving colouring of the binder or support material, for example iron oxide or chromium oxide pigments, or else phthalocynaine or azo dyestuff.

Preferred water binders which are optionally incorporated into the support materials/binders are zeolites.

Examples of suitable surfactants are cellulose powder, active charcoal and silica gels.

Especially preferred are emulsion polymerisates such as, for example, polyvinyl chloride, polylactides, polystyrene, polyvinyl acetates, polybutadiene, polyacrylonitrile, polyvinyl esters, polyvinyl ethers, and copolymers of these.

Very especially preferred are emulsion-polymerized copolymerisates of methyl and ethyl esters of acrylic acid and methacrylic acid.

To prepare the binders/support materials/shaped articles/implants according to the invention, the individual components can be mixed in the dry state by customary mixing processes and shaped by customary shaping methods, such as, for example, extruding or injection moulding.

Alternatively, it is possible to dissolve the individual components in suitable solvents and to “spin” them out of the solution by customary methods.

The solid shaped plant treatment products according to the invention are suitable for applying determined amounts of active compound in plants of virtually all genera, in particular in the domestic and horticultural sectors, in public gardens and in forests.

The process according to the invention is suitable for the treatment of individual plants, preferably of herbaceous plants, annual or perennial shrubs, and of woody species such as bushes and trees.

The solid shaped plant treatment products according to the invention generally comprise between 10% and 90%, preferably between 50% and 75%, of herbicidally active compound and between 90% and 10%, preferably between 50% and 25%, of binder.

Preparation and use of the plant treatment products according to the invention are described hereinbelow by way of examples.

Preparation examples/formulation examples:

EXAMPLE 1

To prepare active-compound-comprising shaped articles according to the invention, 50 parts by weight of glyphosate and 50 parts by weight of the polymeric support material polyethylene oxide WSR N 80 are metered separately via differential scales into the feed zone of a twin-screw extruder, type ZSK 32 (Werner & Pleiderer). In the extruder, the components are homogenized in the course of 4 minutes at 100° C. to 130° C., the melt is extruded at a throughput of ⅛ kg/h, air-cooled and granulated. After granulation, the active-compound-comprising composition is shaped into rods, bars, strips or slabs at 120° C. with the aid of a press.

EXAMPLE 2

In analogy to Example 1, 50 parts by weight of glufosinate and 50 parts by weight of the polymeric support material polyethylene oxide WSR N 80 are extruded and processed to give shaped articles.

EXAMPLE 3

In analogy to Example 1, 50 parts by weight of sulphosate and 50 parts by weight of the polymeric support material polyethylene oxide WSR N 80 are extruded and processed to give shaped articles.

EXAMPLE 4

In analogy to Example 1, 50 parts by weight of bialaphos and 50 parts by weight of the polymeric support material polyethylene oxide WSR N 80 are extruded and processed to give shaped articles.

EXAMPLE 5

In analogy to Example 1, 50 parts by weight of glufosinate and 50 parts by weight of a copolymer of N-vinylpyrrolidine and vinyl acetate (Luviskol VA 64) are extruded at 80° C. to 130° C. and processed to give shaped articles.

EXAMPLE 6

50 parts by weight of a blend of starch and poly-ϵ-caprolactone (MaterBi) are extruded in analogy to Example 1 with 50 parts by weight of bialaphos at 100° C. to 160° C. to give an extrudate/cable. The cable is subsequently cut into bars 2 cm in length.

EXAMPLE 7

50 parts by weight of a cellulose hydroxypropyl phthalate with a mean degree of substitution (average number of grafted monomers per glucose unit) of 2.36 and a mean degree of substitution (average number of derivatized OH groups per glucose unit) of 1.80 are extruded in analogy to Example 1 with 50 parts by weight of glyphosate at 100° C. to 160° C., air-cooled and granulated. The granules are subsequently processed in an Arburg Allrounder type injection moulding machine (nozzle temperature: 130° C., tool temperature: 30° C.) to give nail-like implants.

EXAMPLE 8

A mixture of 255 parts by weight of polyvinyl alcohol Mowiol 4-88 and 45 parts by weight of glycerol is molten in a type Haake Rheomix kneader at 130° C. and 50 rpm, and 100 parts by weight of sulphosate subsequently added. To homogenize the batch, it is kneaded for 15 minutes. The resulting composition is processed in a press at 200 bar/120° C. to give slabs of an area of 100 $cm^2$ and a thickness of 2 mm.

EXAMPLE 9

To prepare other active-compound-comprising shaped articles according to the invention, 50 parts by weight of N-phosphonomethyl-glycine ethyl ester and 50 parts by weight of the polymeric support material polyethylene oxide WSR N 80 are metered separately via differential scales into the feed zone of a ZSK 32 type twin-screw extruder (Werner & Pleiderer). In the extruder, the components are homogenized in the course of 4 minutes at 100° C. to 130° C., the melt is extruded at a throughput of 1.8 kg/h, air-cooled and granulated. After granulation, the active-compound-comprising composition is shaped into rods, bars, strips or slabs at 120° C. with the aid of a press.

EXAMPLE 10

In analogy to Example 9, 50 parts by weight of N-phosphonomethyl-glycine ethyl ester and 50 parts by weight of a copolymer of N-vinyl-pyrrolidine and vinyl acetate (Luviskol VA 64) are extruded at 80° C. to 130° C. and processed to give shaped articles.

EXAMPLE 11

50 parts by weight of a blend of starch and poly-ϵ-caprolactone (MaterBi) are extruded in analogy to Example 9 with 50 parts by weight of N-phosphonomethyl-gylcin ethyl ester at 100° C. to 160° C. to give an extrudate/cable. The cable is subsequently cut into bars 2 cm in length.

EXAMPLE 12

50 parts by weight of a cellulose hydroxypropyl phthalate with a mean degree of substitution (average number of grafted monomers per glucose unit) of 2.36 and a mean degree of substitution (average number of derivatized OH groups per glucose unit) of 1.80 are extruded in analogy to Example 9 with 50 parts by weight of N-phosphonomethyl-gylcin ethyl ester at 100° C. to 160° C., air-cooled and granulated. The granules are subsequently processed in an Arburg Allrounder type injection moulding machine (nozzle temperature: 130° C., tool temperature: 30° C.) to give nail-like implants.

EXAMPLE 13

A mixture of 255 parts by weight of polyvinylalcohol Mowiol 4-88 and 45 parts by weight of glycerol is molten in a Haake Rheomix type kneader at 130° C. and 50 rpm, and 100 parts by weight of N-phosphonomethyl-gylcin ether ester subsequently added. To homogenize the batch, it is kneaded for 15 minutes. The resulting composition is processed in a press at 200 bar/120° C. to give slabs of an area of 100 $cm^2$ and a thickness of 2 mm.

Use examples:

EXAMPLE A

The treatment is performed on test plants (birches; elder) of a height of 3 m to 6 m and a trunk circumference of 5 cm to 30 cm. The shaped articles according to the invention ("implants") are inserted flush into pre-drilled holes (diameter approx. 6 mm, depth approx. 16 mm), 1 implant (approx. 0.5 g comprising approx. 0.30 g of active compound) being used per cm of trunk circumference.

After 4 weeks, the degree of damage to the plants is scored (% damage in comparison with untreated control).

In this test, for example the compound N-phosphonomethyl-glycine i-propylamine salt used in accordance with the above description shows complete destruction of the test plants.

EXAMPLE B

The treatment is performed on test plants (birches; elder) of a height of 3 m to 6 m and a trunk circumference of 5 cm to 30 cm. The shaped articles according to the invention ("implants") are inserted flush into pre-drilled holes (diameter approx. 6 mm, depth approx. 16 mm), 1 implant (approx. 0.5 g comprising approx. 0.30 g of active compound) being used per cm of trunk circumference.

After 4 weeks, the degree of damage to the plants is scored (% damage in comparison with untreated control).

In this test, for example the compound N-phosphonomethyl-gylcin ethyl ester used in accordance with the above description shows complete destruction of the test plants.

Examples for the preparation of active compounds:

EXAMPLE 1

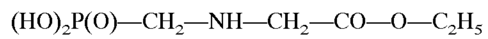

$(HO)_2P(O)—CH_2—NH—CH_2—CO—O—C_2H_5$

Hydrogen chloride gas is passed to saturation into a suspension of 200 g (1.2 mol) of N-phosphonomethyl-glycine in 3000 ml of ethanol. The reaction mixture is then refluxed for 3 hours and subsequently—after having been cooled to room temperature—concentrated under a water pump vacuum. The residue is dissolved in 1500 ml of ethanol, and triethylamine (approx. 140 g) is added dropwise to this solution until the colour changes from reddish-brown to pale yellow. The crystalline product obtained is isolated by filtration under suction.

This gives 201 g (85% of theory) of N-phosphonomethyl-glycine ethyl ester of melting point >220° C.

"Drying" of the product obtained in accordance with Example 1—i.e. removal of the alcohol—can be effected, for example, by the following methods conventionally used in the art, if appropriate in combination with comminution methods conventionally used in the art:

fluidized-bed drying, puddle drying or recirculating-air drying (if appropriate in each case in combination with comminution methods conventionally used in the art such as, for example, air-jet grinding, crushers, rollers, grinding).

EXAMPLE 2

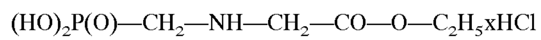

$(HO)_2P(O)—CH_2—NH—CH_2—CO—O—C_2H_5xHCl$

Hydrogen chloride gas is passed to saturation into a suspension of 5.1 g (30 mmol) of N-phosphonomethyl-glycine in 80 ml of ethanol. The reaction mixture is then refluxed for 2 hours and subsequently concentrated under a rotor pump vacuum. The residue is stirred with acetone and the crystalline product is isolated by filtration with suction.

This gives 3.0 g (43% of theory) of N-phosphonomethyl-glycine ethyl ester hydrochloride in the form of hydroscopic crystals which liquify upon heating.

What is claimed is:

1. A method for the destruction of trees and shrub-like plants with a systemically active herbicide, comprising the step of introducing into the trees or shrub-like plants a solid, rod-shaped plant treatment product which consists of:

a systemic herbicide comprising glyphosate or a salt thereof, wherein said herbicide is homogeneously distributed in a polymeric carrier material, and wherein said carrier material is soluble in the sap of plants, and is selected from the group consisting of polyethylene oxide, a copolymer of N-vinylpyrrolidone and vinyl acetate, and a mixture of polyvinyl alcohol and glycerol.

* * * * *